United States Patent [19]

Domagala et al.

[11] Patent Number: 5,116,834
[45] Date of Patent: May 26, 1992

[54] QUINOLINECARBOXYLIC ACID ANTIBACTERIAL AGENTS

[75] Inventors: John M. Domagala, Canton; Mark J. Suto; William R. Turner, both of Ann Arbor, all of Mich.

[73] Assignee: Warner-Lambert Company, Morris Plains, N.J.

[21] Appl. No.: 687,254

[22] Filed: Apr. 18, 1991

Related U.S. Application Data

[62] Division of Ser. No. 508,886, Apr. 12, 1990, Pat. No. 5,047,538.

[51] Int. Cl.$^5$ .................. A61K 31/55; A61K 31/47; A61K 31/495; C07D 401/10

[52] U.S. Cl. .................. 514/212; 514/214; 514/254; 514/312; 540/520; 540/579; 540/597; 544/363; 546/156; 560/8; 560/47; 560/104; 562/405; 562/456; 562/495

[58] Field of Search .................. 546/156; 514/312; 540/597

[56] References Cited

U.S. PATENT DOCUMENTS 4,894,458  1/1990  Masuzawa et al. .................. 546/156

*Primary Examiner*—Nicholas S. Rizzo
*Assistant Examiner*—E. Bernhardt
*Attorney, Agent, or Firm*—Ronald A. Daignault

[57] ABSTRACT

Novel 8-alkenyl, alkynyl, allenyl and cycloalkyl-quinolinecarboxylic acids are described as antibacterial agents as well as methods of manufacture including novel intermediates used in said manufacture.

13 Claims, No Drawings

QUINOLINECARBOXYLIC ACID ANTIBACTERIAL AGENTS

This is a divisional of U.S. patent application Ser. No. 508,886 filed Apr. 12, 1990 now U.S. Pat. No. 5,047,538.

BACKGROUND OF THE INVENTION

While 8-alkylquinolinecarboxylic acids have been described n the literature as having antibacterial activity, the present 8-alkenyl, alkynyl, and cycloalkyquinolinecarboxylic acids provide novel antibacterial agents.

SUMMARY OF THE INVENTION

Accordingly, the present invention in a first aspect is a compound of Formula I

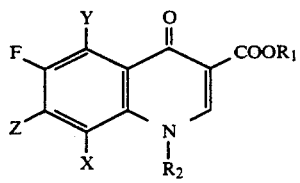

wherein
X is alkenyl, alkynyl, allenyl, cycloalkyl, or alkylsubstituted cycloalkyl;
Y is hydrogen, fluoro, or amino;
Z is a secondary cyclic amino group of the formulae

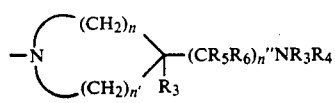

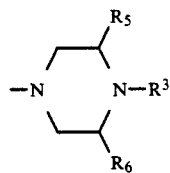

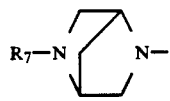

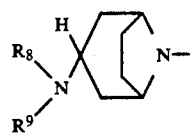

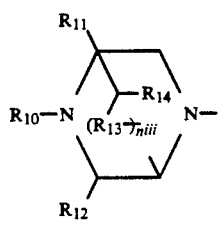

or

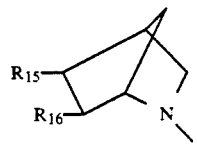

wherein
n is 1, 2, 3, or 4;
n' is 1, 2, 3, or 4;
n+n' is a total of 2, 3, 4, or 5;
n'' is 0, 1, or 2;
n''' is 0 or 1;
$R_1$ is hydrogen, an alkyl of from one to six carbon atoms or a cation;
$R_2$ is alkyl of from one to four carbon atoms, vinyl, haloalkyl, or hydroxyalkyl of from one to four carbon atoms, cycloalkyl of from three to six carbon atoms, or phenyl or phenyl substituted by one or more halogen atoms;
$R_3$ is hydrogen, alkyl of from one to four carbon atoms, or a cycloalkyl of from three to six carbon atoms;
$R_4$ is hydrogen, alkyl of from one to four carbon atoms, hydroxyalkyl of from two to four carbon atoms, trifluoroethyl, or $R'_4CO$ wherein $R'_4$ is alkyl of from one to four carbon atoms, or alkoxy of from one to four carbon atoms;
$R_5$ and $R_6$ are each independently hydrogen or alkyl of from one to three carbon atoms;
$R_7$ is hydrogen, alkyl of from one to three carbon atoms, hydroxyalkyl of from two to three carbon atoms, benzyl, or p-aminobenzyl;
$R_8$ and $R_9$ are each independently hydrogen, alkanoyl of from one to three carbon atoms, alkyl of from one to three carbon atoms, isopropyl, or cyclopropyl;
$R_{10}$ and $R_{11}$ are each independently hydrogen, methyl, ethyl, or benzyl;
$R_{12}$, $R_{13}$, and $R_{14}$ are each independently hydrogen or methyl;
$R_{15}$ and $R_{16}$ are each independently hydrogen, halogen, $NR_{17}R_{18}$, $OR_{17}$, $SR_{17}$, alkyl of from one to three carbon atoms, wherein $R_{17}$ and $R_{18}$ are each independently hydrogen, alkyl of from one to three carbon atoms, or alkanoyl of from one to three carbon atoms;
or a pharmaceutically acceptable acid addition or base salt thereof.

Another aspect of the invention is a process for preparing compounds of Formula I

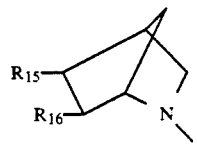

wherein Y, Z, X, $R_1$, and $R_2$ are as defined above by reacting a compound of Formula IV (hereinafter shown), where $Z^1$ is a halogen atom, with an appropriate secondary amine.

Certain novel intermediates in the process for preparing a compound of Formula I are also included in the present invention. They include a compound of Formula II

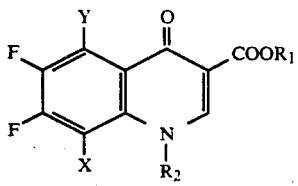

wherein X, Y, R$_1$, and R$_2$ are as defined above and a compound of Formula III

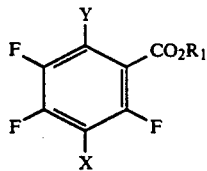

wherein X, Y, and R$_1$ are as defined above

The invention also includes a pharmaceutical composition which comprises an antibacterially effective amount of a compound of Formula I or a pharmaceutically acceptable salt thereof in combination with a pharmaceutically acceptable carrier.

The invention further includes a method for treating bacterial infections in mammals which comprises administering an antibacterially effective amount of the above defined pharmaceutical composition to a mammal in need thereof.

DETAILED DESCRIPTION OF PREFERRED EMBODIMENTS

Substituents for the compounds of Formula I are defined hereafter.

The alkyl groups contemplated by the invention comprise both straight and branched carbon chains of from one to about six carbon atoms. Representative of such groups are methyl, ethyl, propyl, isopropyl, n-butyl, sec-butyl, isobutyl, tertiary-butyl, and the like.

The alkenyl groups contemplated by the invention comprise both straight and branched carbon chains of from two to ten carbon atoms. Representative of such groups are ethenyl, 1-propenyl, 2-propenyl, 1-butenyl, 2-butenyl, 3-butenyl, 2-methyl-1-propenyl, and the like.

The alkynyl groups contemplated by the invention comprise a carbon chain of from two to eight carbon atoms. Representative of such groups are ethynyl, 1-propynyl, 2-propynyl, and the like.

The allenyl groups contemplated by the invention comprise a carbon chain of from three to ten carbon atoms containing two consecutive double bonded carbon atoms. Representative of such groups are allene, and the like.

The cycloalkyl groups contemplated by the invention comprise those having three to six carbon atoms such as cyclopropyl, cyclobutyl, cyclopentyl, and cyclohexyl.

The term alkanoyl is intended to include

groups wherein R$^1$ is an alkyl of from one to three carbon atoms.

The hydroxyalkyl groups contemplated by the invention comprise those having two to four carbon atoms such as 2-hydroxyethyl, 2- or 3-hydroxypropyl, or 2-, 3-, or 4-hydroxybutyl.

The alkoxy groups contemplated by the invention comprise both straight and branched carbon chains of from one to about six carbon atoms. Representative of such groups are methoxy, ethoxy, propoxy, i-propoxy, t-butoxy, hexoxy, and the like.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2propyl, and the like.

The term halogen is intended to include fluorine, chlorine, bromine, and iodine.

Certain compounds of the invention may exist in optically active forms. The pure R isomer, pure S isomer as well as mixtures thereof, including the racemic mixtures, are contemplated by the invention. Additional asymmetric carbon atoms may be present in a substituent such as an alkyl group. All such isomers as well as mixtures thereof are intended to be included in the invention. Certain side chains may contain more than one chiral center. In these cases the diasteroisomers may be separated and utilized individually. All such mixtures and separated mixtures are contemplated by the invention.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as, for example, silver, zinc, cobalt, and cerium. Such heavy metal salts are effective in the treatment of burns, especially when applied to the affected surface of a burn victim either directly or in combination with a physiologically acceptable carrier such as a water dispersible, hydrophilic carrier. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, lactic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The preferred compounds of this invention are those of Formula I wherein Y is hydrogen or amino and $R_2$ is ethyl, vinyl, 2-fluoroethyl, difluoroethyl, cyclopropyl, phenyl, 2-fluorophenyl, 4-fluorophenyl, or 2,4-difluorophenyl.

Also preferred compounds of this invention are those wherein Z is

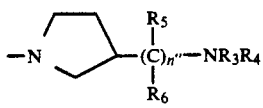

or

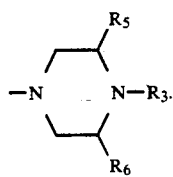

Other preferred compounds of this invention are those wherein $R_1$ is hydrogen or a pharmaceutically acceptable base salt such as a metal or an amine salt.

Other preferred compounds of this invention are those wherein $n''$ is zero or one, $R_3$, $R_5$, and $R_6$ are hydrogen, methyl, ethyl, or n-propyl, and $R_4$ is hydrogen.

The most preferred compounds are those wherein Z is

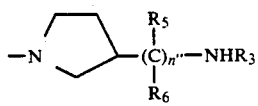

or

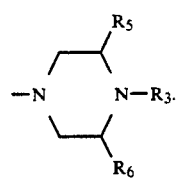

wherein $R_1$ is hydrogen, $R_2$ is ethyl, vinyl, 2-fluoroethyl, cyclopropyl, or 2,4-difluorophenyl, and $R_3$ is hydrogen, methyl, ethyl, 1-propyl, 2-propyl, $R_5$, $R_6$ are hydrogen or methyl, or a pharmaceutically acceptable acid addition or base salt thereof.

Additionally, the most preferred compounds include those wherein $R_2$ is cyclopropyl, Z is

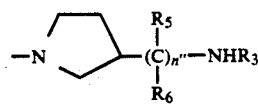

in which $n''$ is 0 or 1 and $R_3$ is hydrogen, methyl, ethyl, 1-propyl, 2-propyl, $R_5$ and $R_6$ are hydrogen or methyl, and $R_1$ is hydrogen or a pharmaceutically acceptable base salt thereof.

Of the most preferred compounds of Formula I mentioned above, valuable are those wherein X is alkenyl of from two to ten carbon atoms, alkynyl of from two to eight carbon atoms or cycloalkyl of from three to six carbon atoms. More valuable are those compounds of Formula I wherein X is alkenyl from two to four carbon atoms, alkynyl of from two to three carbon atoms, cyclobutyl or cyclopropyl. Most valuable are those compounds of Formula I wherein X is ethenyl, ethynyl or cyclopropyl.

Particularly preferred compounds of the present invention are:

1-cyclopropyl-8ethenyl-6-fluoro-1,4-dihydro-7-(3-methyl-1-piperazinyl)-4-oxo-3-quinolinecarboxylic acid;

1-cyclopropyl-8-ethenyl-7-[3(S)-ethylamino)methyl-1-pyrrolidine]-6-fluoro-1,4-dihydro-4-oxo-3-quinolinecarboxylic acid;

1-cyclopropyl-8-ethenyl-6-fluoro-1,4-dihydro-4-oxo-7-(1-piperazinyl)-3-quinolinecarboxylic acid;

7-(3-amino-1-pyrrolidinyl)-1-cyclopropyl-8-ethenyl-6-fluoro-1,4-dihydro-4-oxo-3-quinolinecarboxylic acid;

1-cyclopropyl-8-ethenyl-6-fluoro-1,4-dihydro-7-[3-[methylamino)methyl]-1-pyrrolidinyl]-4-oxo-3-quinolinecarboxylic acid;

1-cyclopropyl-8-ethenyl-7-[3-[(ethylamino)methyl]-1-pyrrolidinyl]-6-fluoro-1,4-dihydro-4-oxo-3-quinolinecarboxylic acid;

7-(3-amino-1-piperidinyl)-1-cyclopropyl-8-ethenyl-6-fluoro-1,4-dihydro-4-oxo-3-quinolinecarboxylic acid;

1-cyclopropyl-8-ethenyl-6-fluoro-1,4-dihydro-4-oxo-7-(1-piperazinyl)-3-quinolinecarboxylic acid;

1-cyclopropyl-7-(2,5-diazabicyclo[2.2.1]hept-2-yl)-8-ethenyl-6-fluoro-1,4-dihydro-4-oxo-3-quinolinecarboxylic acid;

7-[3-(1-aminoethyl)-1-pyrrolidinyl]-1-cyclopropylpropyl-8-ethenyl-6-fluoro-1,4-dihydro-4-oxo-3-quinolinecarboxylic acid, all isomers;

7-(3-amino-1-pyrrolidinyl)-1-(2,4-difluorophenyl)-8-ethenyl-6-fluoro-1,4-dihydro-4-oxo-3-quinolinecarboxylic acid;

1-(2,4-difluorophenyl)-8-ethenyl-6-fluoro-1,4-dihydro-7-[3-[(methylamino)methyl]-1-pyrrolidinyl]-4-oxo-3-quinolinecarboxylic acid;

1-(2,4-difluorophenyl)-8-ethenyl-7-[3-[(methylamino)-methyl]-1-pyrrolidinyl]-4-oxo-3-quinolinecarboxylic acid;

7-(3-amino-1-piperidinyl)-1-(2,4-difluorophenyl)-8-ethenyl-6-fluoro-1,4-dihydro-4-oxo-3-quinolinecarboxylic acid;

1-(2,4-difluorophenyl)-8-ethenyl-6-fluoro-1,4-dihydro-4-oxo-7 (1-piperazinyl)-3-quinolinecarboxylic acid;

1-(2,4-difluorophenyl)-8-ethenyl-6-fluoro-1,4-dihydro-7-(3-methyl-1-piperazinyl)-4-oxo-3-quinoline-carboxylic acid;

7-(2,5-diazabicyclo[2.2.1]hept-2-yl)-1-(2,4-difluorophenyl)-8-ethenyl-6-fluoro-1,4-dihydro-4-oxo-3-quinolinecarboxylic acid;

7-[3-(1-aminoethyl)-1-pyrrolidinyl]-1-(2,4-difluorophenyl)-8-ethenyl-6-fluoro-1,4-dihydro-4-oxo-3-quinolinecarboxylic acid, all isomers;

7-(3-amino-1-pyrrolidinyl)-1,8-dicyclopropyl-6-fluoro-1,4-dihydro-4-oxo-3-quinolinecarboxylic acid;

1,8-dicyclopropyl-6-fluoro-1,4-dihydro-7-[3-[(methylaminomethyl]-1-pyrrolidinyl]-4-oxo-3-quinolinecarboxylic acid;

1,8-dicyclopropyl-7-[3-[(ethylamino)methyl]-1-pyrrolidinyl]6-fluoro-1,4-dihydro-4-oxo-3-quinolinecarboxylic acid;

7-(3-amino-1-piperidinyl)-1,8-dicyclopropyl-6-fluoro-1,4-dihydro-4-oxo-3-quinolinecarboxylic acid;

1,8-dicyclopropyl-6-fluoro-1,4-dihydro-7-(1-piperazinyl)-4-oxo-3-quinolinecarboxylic acid;

1,8-dicylopropyl-6-fluoro-1,4-dihydro-4-oxo-7-(3-methyl-1-piperazinyl)-3-quinolinecarboxylic acid;

1,8-dicyclopropyl-7-(2,5-diazabicyclo[2.2.1]hept-2-yl)-6-fluoro-1,4-dihydro-4-oxo-3-quinolinecarboxylic acid;

7-[3-(1-aminoethyl)-1-pyrrolidinyl]-1,8-dicyclopropyl-6-fluoro-1,4-dihydro-4-oxo-3-quinolinecarboxylic acid;

7-(3-amino-1-pyrrolidinyl)-8-cyclopropyl-1-(2,4-difluorophenyl)-6-fluoro-1,4-dihydro-4-oxo-3-quinolinecarboxylic acid;

8-cyclopropyl-1-(2,4-difluorophenyl)-6-fluoro-1,4-dihydro-7-[3-[(methylamino)methyl]-1-pyrrolidinyl]-4-oxo-3-quinolinecarboxylic acid;

8-cyclopropyl-1-(2,4-difluorophenyl)-7-[3-[ethylamino)methyl]-1-pyrrolidinyl]-6-fluoro-1,4-dihydro-4-oxo-3-quinolinecarboxylic acid;

7-(3-amino-1-piperidinyl)-8-cyclopropyl-1-(2,4-difluorophenyl)-6-fluoro-1,4-dihydro-4-oxo-3-quinolinecarboxylic acid;

8-cyclopropyl-1-(2,4-difluorophenyl)-6-fluoro-1,4-dihydro-4-oxo-7-(1-piperazinyl)-3-quinolinecarboxylic acid;

8-cyclopropyl-1-(2,4-difluorophenyl)-6-fluoro-1,4-dihydro-7-(3-methyl-1-piperazinyl)-4-oxo-3-quinolinecarboxylic acid;

8-cyclopropyl-7-(2,5-diazabicyclo[2.2.1]hept-2-yl)-1-(2,4-difluorophenyl)-6-fluoro-1,4-dihydro-4-oxo-3-quinolinecarboxylic acid;

7-[3-(1-aminoethyl)-1-pyrrolidinyl]-8-cyclopropyl-1-(2,4-difluorophenyl-6-fluoro-1,4-dihydro-4-oxo-3-quinolinecarboxylic acid;

7-(3-amino-1-pyrrolidinyl)-1-cyclopropyl-6-fluoro-1,4dihydro-8-(1-methylethenyl)-4-oxo-3-quinolinecarboxylic acid;

1-cyclopropyl-6-fluoro-1,4-dihydro-7-[3-[(methylamino)methyl]-1-pyrrolidinyl]-8-(1-methylethenyl)-4-oxo-3-quinolinecarboxylic acid;

1-cyclopropyl-7-[3-[(ethylamino)methyl]-1-pyrrolidinyl]-6-fluoro-1,4-dihydro-8-(1-methylethenyl)-4-oxo-3-quinolinecarboxylic acid;

7-(3-amino-1-piperidinyl)-1-cyclopropyl-6-fluoro-1,4-dihydro-8-(1-methylethenyl)-4-oxo-3-quinolinecarboxylic acid;

1-cyclopropyl-6-fluoro-1,4-dihydro-8-(1-methylethenyl)-4-oxo-7-(1-piperazinyl)-3-quinolinecarboxylic acid;

1-cyclopropyl-6-fluoro-1,4-dihydro-8-(1-methylethenyl)-7-(3-methyl-1-piperazinyl)-4-oxo-3-quinoline carboxylic acid;

1-cyclopropyl-7-(2,5-diazabicyclo[2.2.1]hept-2-yl)-6-fluoro-1,4-dihydro-8-(1-methylethenyl)-4-oxo-3-quinolinecarboxylic acid;

7-[3-(1-aminoethyl)-1-pyrrolidinyl]-1-cyclopropyl-6-fluoro-1,4-dihydro-8-(1-methylethenyl)-4-oxo-3-quinolinecarboxylic acid;

7-(3-amino-1-pyrrolidinyl)-1-(2,4-difluorophenyl)-6-fluoro-1,4-dihydro-8-(1-methylethenyl)-4-oxo-3-quinolinecarboxylic acid;

1-(2,4-difluorophenyl)-6-fluoro-1,4-dihydro-7-[3-[(methylamino)methyl]-1-pyrrolidinyl]-8-(1-methylethenyl)-4-oxo-3-quinolinecarboxylic acid;

1-(2,4-difluorophenyl)-7-[3-[(ethylamino)methyl]-1-pyrrolidinyl]-6-fluoro-1,4-dihydro-8-(1-methylethenyl)-4-oxo-3-quinolinecarboxylic acid;

7-(3-amino-1-piperidinyl)-1-(2,4-difluorophenyl)-6-fluoro-1,4-dihydro-8-(1-methylethenyl)-4-oxo-3-quinolinecarboxylic acid;

1-(2,4-difluorophenyl)-6-fluoro-1,4-dihydro-8-(1-methylethenyl)-4-oxo-7-(1-piperazinyl)-3-quinolinecarboxylic acid;

1-(2,4-difluorophenyl)-6-fluoro-1,4-dihydro-8-(1-methylethenyl)-7-(3-methyl-1-piperazinyl)-4-oxo-3-quinolinecarboxylic acid;

7-(2,5-diazabicyclo[2.2.1]hept-2-yl)-1-(2,4-difluorophenyl)-6-fluoro-1,4-dihydro-8-(1-methylethenyl)-4-oxo-3-quinolinecarboxylic acid;

7-[3-(1-aminoethyl)-1-pyrrolidinyl]-1-(2,4-difluorophenyl)-6-fluoro-1,4-dihydro-8-(1-methylethenyl)-4-oxo-3-quinolinecarboxylic acid;

7-(3-amino-1-pyrrolidinyl)-1-cyclopropyl-8-ethynyl-6-fluoro-1,4-dihydro-4-oxo-3-quinolinecarboxylic acid;

1-cyclopropyl-8-ethynyl-6-fluoro-1,4-dihydro-7-[3-[(methylamino)methyl]-1-pyrrolidinyl]-4-oxo-3-quinolinecarboxylic acid;

1-cyclopropyl-7-[3-[(ethylamino)methyl]-1-pyrrolidinyl]-8-ethynyl-6-fluoro-1,4-dihydro-4-oxo-3-quinolinecarboxylic acid;

7-(3-amino-1-piperidinyl)-1-cyclopropyl-8-ethynyl-6-fluoro-1,4-dihydro-4-oxo-3-quinolinecarboxylic acid;

1-cyclopropyl-8-ethynyl-6-fluoro-1,4-dihydro-4-oxo-7-(1-piperazinyl)-3-quinolinecarboxylic acid;

1-cyclopropyl-8-ethynyl-6-fluoro-1,4-dihydro-4-oxo-7-(3-methyl-1-piperazinyl)-4-oxo-3-quinolinecarboxylic acid;

1-cyclopropyl-7-(2,5-diazabicyclo[2.2.1]hept-2-yl)-8-ethynyl-6-fluoro-1,4-dihydro-4-oxo-3-quinolinecarboxylic acid;

7[3-(1-aminoethyl)-1-aminoethyl)-1-pyrrolidinyl]-1-cyclopropyl-8-ethynyl-6-fluoro-1,4-dihydro-4-oxo-3-quinolinecarboxylic acid;

7-(3-amino-1-pyrrolidinyl)-1-(2,4-difluorophenyl)-8-ethynyl-6-fluoro-1,4-dihydro-4-oxo-3-quinolinecarboxylic acid;

1-(2,4-difluorophenyl)-8-ethynyl-6-fluoro-1,4-dihydro-7-[3-[(methylamino)methyl]-1-pyrrolidinyl]-4-oxo-3-quinolinecarboxylic acid;

1-(2,4-difluorophenyl)-7-[3-[(ethylamino)methyl]-1-pyrrolidinyl]-8-ethynyl-6-fluoro-1,4-dihydro-4-oxo-3-quinolinecarboxylic acid;

7-(3-amino-1-piperidinyl)-1-(2,4-difluorophenyl)-8-ethynyl-6-fluoro-1,4-dihydro-4-oxo-3-quinolinecarboxylic acid;

1-(2,4-difluorophenyl)-8-ethynyl-6-fluoro-1,4-dihydro-4-oxo-7-(1-piperazinyl)-3-quinolinecarboxylic acid;

1-(2,4-difluorophenyl)-8-ethynyl-6-fluoro-1,4-dihydro-7-(3-methyl-1-piperazinyl)-4-oxo-3-quinolinecarboxylic acid; 7-(2,5-diazabicyclo[2.2.1]hept-2-yl)-1-(2,4-difluorophenyl)-8-ethynyl-6-fluoro-1,4-dihydro-4-oxo-3-quinolinecarboxylic acid; and 7-[3-(1-aminoethyl)-1-pyrrolidinyl]-1-(2,4-difluorophenyl)-8-ethynyl-6-fluoro-1,4-dihydro-4-oxo-3-quinolinecarboxylic acid.

The compound of the present invention and of Formula I may be prepared generally by reacting a compound of the Formula IV

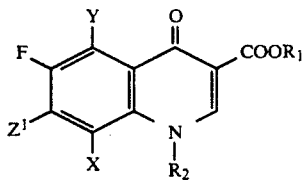

IV wherein X, Y, R₁, and R₂ are as defined above and Z¹ is a halogen atom, preferably fluorine, with an appropriate secondary amine, ZH, wherein Z is as defined above, and, if desired, converting by known methods the resulting free zwitterion or ester to a free acid or a pharmaceutically acceptable acid addition or base salt thereof.

Starting from a readily available starting material, the compounds of Formula I may be prepared by (a) reacting 3-hydroxy-2,4,5-trifluoro benzoic acid with triflic anhydride, followed by reaction with the appropriate tin reagent, for example, under palladium catalysis to form for example, 2,4,5-trifluoro-3-vinyl-benzoic acid;

(b) reacting the above benzoic acid with an activating group, for example, oxalyl chloride or carbonyl diimidazole, and an alkyl hydrogen malonate derivative and a base forming as, for example, 2,4,5-trifluoro-β-oxo-3-vinyl benzene propionate;

(c) reacting the above product with alkyl orthoformate and acetic anhydride and the resulting ethoxy methylene β-oxobenzene propionate with a primary amine, R₂NH₂ wherein R₂ is as defined above, forming as, for example, an alkyl α-(N-R₂ aminomethylene)-2,4,5-trifluoro-β-oxo-3-vinyl benzene propionate;

(d) cyclizing the above compound by reacting it with a base in a solvent forming , for example, an alkyl-1-R₂-6,7,-difluoro-1,4,-dihydro-4-oxo-8-vinyl-3-quinoline carboxylate; and (e) reacting the above ester with a secondary amine, ZNH wherein Z is as defined above, and deesterifying the carboxylate forming the corresponding carboxylic acid of Formula I and converting, if desired, the resulting acid to a pharmaceutically acceptable acid addition base salt thereof.

By way of illustration, the following secondary amines may be used in step (a) above to form a compound of Formula I which may be converted, if desired, to a pharmaceutically acceptable acid addition or base salt thereof.

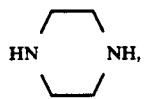

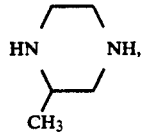

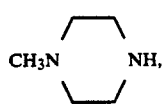

-continued

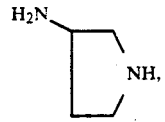

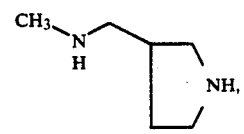

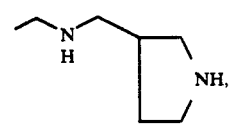

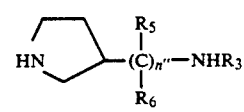

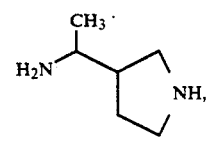

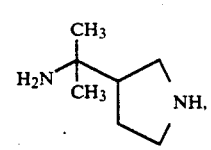

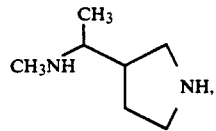

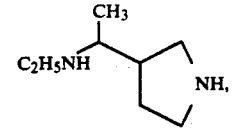

or

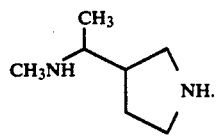

The above secondary amines are either commercially available or can be prepared by known methods from commercially available starting materials.

Some of the above secondary amines have one or two chiral centers and can be resolved into their respective optical isomers and/or separated into their respective diastereoisomers in the case of two chiral centers by known methods as described by Y. Kimura, et al, Abstracts of the 1989 ICAAC meeting, Houston, Tex.

The bicyclic bridged secondary amines are either readily available or may be readily prepared from known starting material by standard procedures or by variations thereof. For example exo- and endo-3-amino-8-azabicyclo[3.2.1]octanes have the structural formula A and the acetyl derivatives B,

A

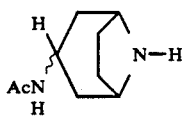

B may be readily prepared from the known starting material 8-(phenylmethyl-8-azabicylco[3.2.1]octan-3-one oxime, [J. R. Bagley and T. N. Riley, *J. Het. Chem.*, 19, 485 (1982)] by the following reaction sequence.

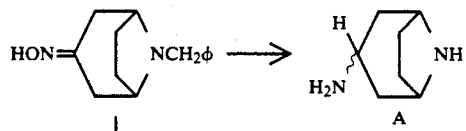

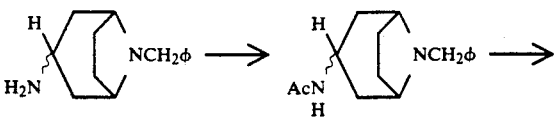

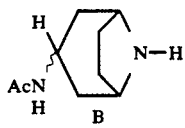

B

Certain compounds of the invention having formula Z wherein Z is

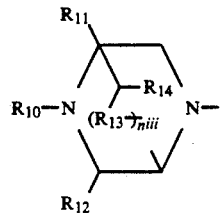

are made by a novel process described hereinafter according to Scheme I below.

Scheme I

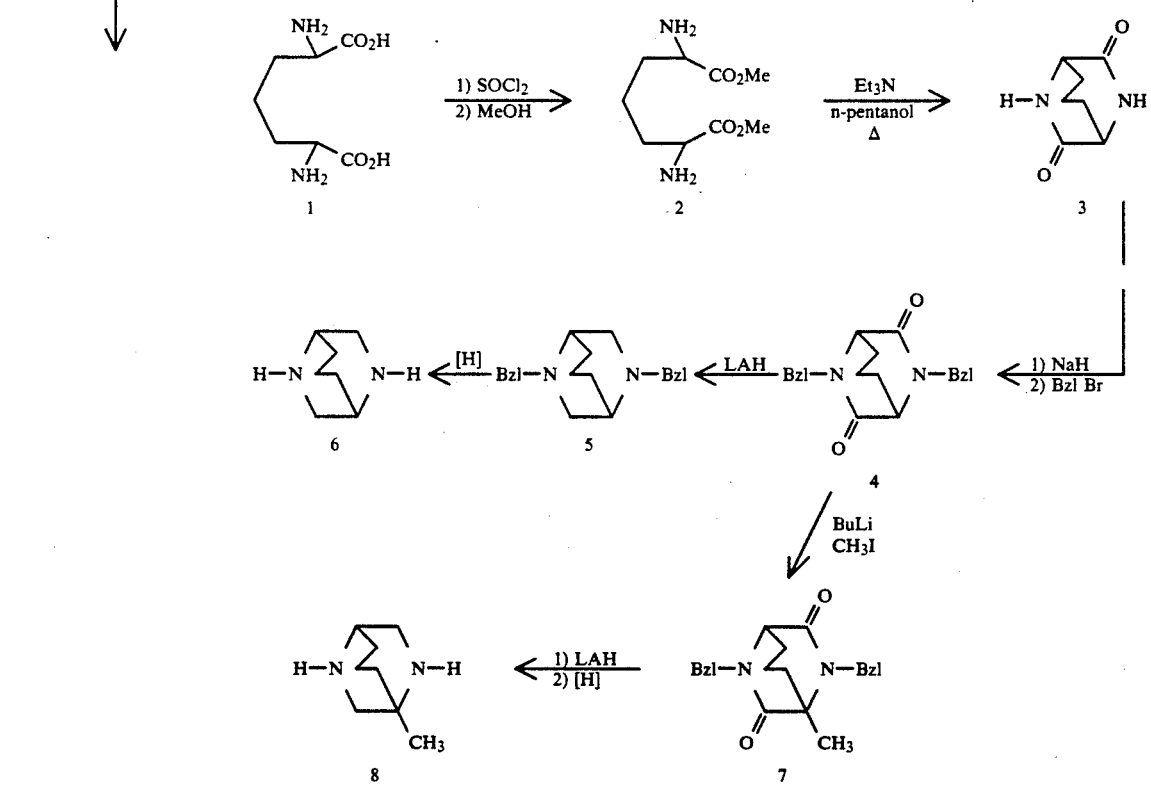

The novel bridged compounds of the present invention are prepared by esterifying a 2,6-diaminoheptanedioic acid (1), preferably with thionyl chloride and methanol, to form the corresponding 2,6-diaminoheptanedioic acid dimethyl ester hydrochloride (2). The 2,6-diaminoheptanedioic acid may be substituted at the 2, 3, or 4-positions each independently by an alkyl, preferably by a methyl group. The reaction proceeds at reflux and then is stirred for from 10 to 20 hours or overnight at room temperature.

The esterified compound is then reacted with a trialkylamine and an alcohol such as, for example, 1-pentanol to form the corresponding 6,8-diazabicyclo-[3.2.2]nonane-7,9-dione (3). The triethylamine is the preferred reactant. A dilute solution is used. It is heated under reflux for as long as 4 days.

The dione formed is reacted with an alkali metal hydride, preferably sodium hydride, and an unsubstituted or substituted benzylhalide to form the corresponding 6,8-bis(substituted or unsubstituted benzyl)-6,8-diazabicyclo[3.2.2]nonane-7,9-dione (4). The benzyl group may be substituted by an alkyl of from one to four, an alkoxy, or a halogen group. The benzyl group methylene may be substituted by alkyl, preferably by a methyl group. Preferably bromomethylbenzene or an α-methyl benzyl halide such as chlorine, bromine, or iodine is used.

Alternatively when it is desired to prepare the dione substituted by, for example, a methyl group, the dione is reacted with butyllithium and an alkyl halide to form the corresponding bridgehead alkyl-substituted 6,8-bis(-substituted phenyl)-6,8-diazabicyclo[3.2.2]-nonane-7,9-dione (7).

The above bis-benzylated dione-containing compound is then reduced to the corresponding 6,8-bis(substituted or unsubstituted benzyl)-6,8-diazabicyclo[3.2.2-]nonane (7 or 5) with lithium aluminum hydride in tetrahydrofuran, diglyme, ether, diethylether or dioxane. Preferably tetrahydrofuran is used. The reduced compound is subsequently debenzylated by catalytic hydrogenation. Preferably palladium on carbon, to form a desired 6,8-diazabicylclo[3.2.2]nonane, hydrochloride (6 or 8). The reaction occurs in methanol and water in a ratio of about 2:1.

Compounds of Formula II wherein $Z^1$ is fluorine are novel and part of the present invention. They are prepared as previously described from compounds of Formula III

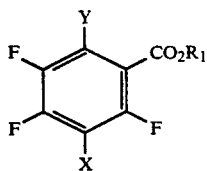

wherein X, Y, and $R_1$ are as defined above. For example, the appropriate carboxylic acid of Formula III is reacted with an activating agent such as carbonyl diimidazole in a solvent such as tetrahydrofuran, THF, at about 25° C. to 40° C. and then treated with the magnesium salt of monoethyl malonate at about 25° C. to 40° C. to provide the desired ethyl 2,4,5-trifluoro-β-oxo-3-(substituted)benzene propionate. Various chlorinating or brominating agents may be used in conjunction with the dianion of ethyl hydrogen malonate at about −78° C. to −40° C.

The above propionate is reacted with an alkyl orthoformate and acetic anhydride and subsequently with a primary alkylamino $R_2NH_2$, forming an ethyl (N-$R^2$ aminomethylene)-3-oxo-3-aryl propionate derivative (5b). The reactants are preferably ethyl orthoformate and cyclopropylamine, ethylamine, or 2,4-difluoroaniline. The reaction proceeds for about 1 to 6 hours at reflux.

The above seco quinolone product is reacted with a base in an organic solvent to cyclize the compound forming alkyl N-$R_2$-6,7-difluoro-8-substituted-quinol-4-one-3-carboxylate. A preferred base is an alkali hydride such as sodium hydride or tertiary amine such as triethylamine and solvents includes but are not limited to t-butanol, DMSO, tetrahydrofuran. The reaction occurs at temperatures from about −20° C. to 100° C.

The resulting quinolone is reacted with a secondary amine, ZNH. Possible reaction solvents include acetonitrile, DMSO or DMF. The reaction proceeds at between 0° C. and 100° C. for a about 2 to 18 hours. Secondary amines reacted with the compound may be protected as necessary. Possible secondary amines include but are not limited to all the secondary amines described above by Z.

The quinoline is then deesterified and, if desired, converted to a pharmaceutically acceptable acid addition or base salt thereof. Useful conditions for deesterifying are sodium hydroxide in alcohol or hydrogen chloride in acetic acid. The deesterification occurs at 25° C. to 40° C. in sodium hydroxide for 18 to 24 hours.

Compounds of Formula III are also novel and form part of the present invention. These compounds may be prepared by a variety of methods from readily available starting materials.

One route involves converting tetrafluorophthalic acid to its corresponding dimethyl ester by standard methods; treating said ester with methanol and base, e.g., potassium carbonate, in dimethylsulfoxide, DMSO, to afford the dimethyl 3,4,6-trifluoro-5-methyoxylphthalate; treating said phthalate with aqueous acid, e.g., sulfuric acid, to provide the 3-hydroxy-2,4,5-trifluorobenzoic acid. This key benzoic acid may be used to prepare the compounds of Formula III.

For example, esterification of the acid and treatment of the hydroxy group with trifluoromethane sulfonyl anhydride provides the 3-trifluoromethyl sulfonyl-2,4,5-trifluoro methyl benzoate. Typical chlorinating agents are oxalyl chloride or thionyl chloride. The reactions are run in inert solvents such as methylene chloride or toluene. Reaction of the ester with trifluoromethanesulfonyl anhydride in pyridine at about 25° C. to 30° C. for about 10 to 18 hours provides the triflate derivative.

The triflate ester is treated with tri-n-butyl vinyltin under palladium catalysis, followed by reaction with a typical base (NaOH) provides 2,4,5-trifluoro-3-vinyl benzoic acid. Typical palladium catalysis are Pd(PPh$_3$)$_4$, Pd(Cl)$_2$(OA$_2$)$_2$. The reactions are run in dioxane, DMF or THF at 40° C. to 120° C. for 10 to 24 hours.

Alternate routes to compounds of Formula III begin with 1-bromo-2,4,5-trifluorobenzene. For example, lithiation of 1-bromo-2,4,5-trifluorobenzene and treatment of the anion with N-formylpiperidine provides 5-bromo-2,3,6-trifluoro benzaldehyde. Typical procedures involve the use of a base, e.g., LDA (lithium diisopropylamide), in THF at about −78° C. to −100° C.

The 5-bromo-2,3,6-trifluorobenzaldehyde may be converted to compounds of Formula III wherein X is alkenyl by treating said aldehyde with the appropriate alkyl triphenyl phosphonium iodide.

Compounds of Formula III where X is alkynyl may be prepared directly from 1-bromo-2,4,5-trifluorobenzene by treating said benzene first in base, e.g., lithium diisopropylamide, at about −78° C. followed with iodine, treating the resulting 1-iodo-2,3,6-trifluoro-5-bromobenzene with trimethylsilylacetylene in the presence of PdCl$_2$ and cuprous iodide in triethylamine at about 25° C., and converting the 1-bromo position to carboxylic acid with, for example, n-butyl lithium and carbon dioxide, then removing the trimethylsilyl group by potassium carbonate in methanol.

The compounds of the invention display anti-bacterial activity when tested by the microtitration dilution method as described in Heifetz, et al, *Antimicr. Agents & Chemoth.*, 6, 124 (1974), which is incorporated herein by reference.

By use of the above reference method, the following minimum inhibitory concentration value (MICs in μg/mL) shown in Table I were obtained for representative compounds of the invention.

TABLE I

| In Vitro Antibacterial Activity Minimal Inhibitory Concentration MIC (μg/mL) | | | |
|---|---|---|---|
| Organism | Ex. 1 | Ex. 2 | Ex. 3 |
| *Enterobacter cloacae* MA 2646 | 0.1 | 0.1 | 0.2 |
| *Escherichia coli* Vogel | 0.1 | 0.1 | 0.1 |
| *Escherichia coli* H56 | 0.05 | 0.05 | 0.1 |
| *Klebsiella pneumoniae* MGH-2 | 0.2 | 0.2 | 0.4 |
| *Proteus rettgeri* M 1771 | 0.4 | 0.4 | 0.4 |
| *Pseudomonas aeruginosa* UI-18 | 1.6 | 1.6 | 3.1 |
| *Staphylococcus aureus* H228 | 0.2 | 0.4 | 0.006 |
| *Staphylococcus aureus* UC-76 | 0.1 | 0.1 | 0.003 |
| *Streptococcus faecalis* MGH-2 | 0.4 | 0.4 | 0.013 |
| *Streptococcus pneumoniae* SV-1 | 0.2 | 0.4 | 0.003 |
| *Streptococcus pyogenes* C-203 | 0.2 | 0.4 | 0.013 |

The compounds of the invention can be prepared and administered in a wide variety of oral, parenteral and topical dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of Formula I with physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is with the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate methods for preparing the compounds of the invention.

PREPARATION OF STARTING MATERIALS

EXAMPLE A

3-Hydroxy-2,4,5-trifluorobenzoic acid methyl ester

A solution of 3-hydroxy-2,4,5-trifluorobenzoic acid (50 g, 0.26 mol) (prepared in an analogous manner to that described in Eur. Pat. Publication 271275) in methylene chloride (500 mL) was added oxalyl chloride (79 g, 0.62 mol). This solution was stirred at room temperature for 18 hours, cooled to 5° C. and then treated dropwise with methanol (100 mL). The mixture was stirred at room temperature for 2 hours, refluxed for 0.5 hour, cooled and concentrated. The residue was partitioned between methylene chloride and saturated sodium bicarbonate. The organic layer was dried (MgSO4) and concentrated to provide 16.7 g of the desired 3-hydroxy-2,4,5-trifluorobenzoic acid methyl ester. Acidification of the bicarbonate layer, extraction with ether and concentration provided an additional 37 g of desired product as indicated by NMR, This material was not purified further but carried into the next step.

EXAMPLE B

2,4,5-Trifluoro-3-trifluoromethylsulfonyl benzoic acid, methyl ester

To a cooled solution (0° to 5° C.) of 3-hydroxy-2,4,5-trifluorobenzoic acid methyl ester (53.7 g, 0.26 mol) in methylene chloride (200 mL) and pyridine (21 g) was added a solution of trifluoromethane sulfonyl anhydride (73 g, 0.26 mol) in methylene chloride (100 mL) dropwise. The reaction was stirred at room temperature for 18 hours at which time an additional 20 g of trifluoromethane sulfonyl anhydride was added. Stirring was continued for 5 additional hours. The reaction was diluted with 10% HCl (500 mL), the organic layer was dried and concentrated. The resulting oil was distilled to provide 77.1 g (88%) of the desired product; bp 80° C. to 100° C. (0.3 mm).

EXAMPLE C

3-Ethenyl-2,4,5-trifluorobenzoic acid

To a solution of 2,4,5-trifluoro-3-trifluoro methanesulfonyl benzoic acid, methyl ester (22.0 g, 0.065 mol) in dioxane (100 mL) was added tri-n-butyl vinyl tin (21.6 g, 0.068 mol), lithium chloride (16.7 g, 0.37 mL) 2,6-di-t-butyl-4-methylphenol (0.08 g) and palladium-tetra-triphenyl phosphine (1.1 g). The mixture was heated at 98° C. for 12 hours, cooled, diluted with ether and filtered through celite. The ether layer was concentrated and the resulting residue suspended in hexane and filtered. The filtrate was concentrated to a yellow oil which was immediately dissolved in methanol (250 mL) and 1N sodium hydroxide (150 mL). The mixture was stirred at room temperature for 4 hours, diluted with water and ether. The aqueous layer was acidified (pH~2) with 6N HCl and extracted with methylene chloride. The organic layer was dried and concentrated to provide the desired product (9.6 g, 77%); mp 108°–110° C.

EXAMPLE D

3-Ethenyl-2,4,5-trifluoro-β-oxo-benzenepropanoic acid, ethyl ester

To a cooled solution (0° to 5° C.) of 3-ethenyl-2,4,5-trifluorobenzoic acid (6.0 g, 0.03 mol) in THF (100 mL) was added carbonyl diimidazole (4.9 g, 0.030 mol). The mixture was then stirred at room temperature for 1 hour, heated with magnesium bis-(ethyl malonate) (8.7 g, 0.03 mol) and refluxed for 3 hours. The reaction was allowed to cool, treated with 3N HCl (30 mL) and stirred for 1.5 hours at room temperature. The reaction was partitioned between ether and water. The organic layer was dried and concentrated to provide 7.65 g (93%) of the desired product. An analytical sample was obtained by preparative TLC (SiO2, 9:1 hexane/EtOAC)

Analysis Calcd: C 57.36, H 4.17, F 20.94
Found: C 57.39, H 4.16, F 21.22.

EXAMPLE E

1-Cyclopropyl-8-ethenyl-6,7-difluoro-1,4-dihydro-4-oxo-3-quinolinecarboxylic acid 3-Ethenyl-2,4,5-trifluoro-β-oxo-benzene propionic acid, ethyl ester (7.1 g, 0.026 mol), ethyl orthoformate (7 mL) and acetic anhydride (4 mL) were refluxed for 6 hours. The volatiles were removed under reduced pressure, and the residual oil was dissolved in THF (50 mL) and treated dropwise with cyclopropylamine (7.98 g, 0.034 mol) in 10 mL of THF at 0° C. The reaction was allowed to warm to room temperature and stirred for 3 hours. The mixture was concentrated, dissolved in ether, filtered, and concentrated to provide 7.6 g (86%) of an oil.

A solution of α-cyclopropylaminomethylene-3-ethenyl-2,4,5-trifluoro-β-oxopropanoic acid, ethyl ester (7.3 g, 0.021 mol) in THF (100 mL) was added dropwise to a cooled solution of NaH (1.1 g, 0.027 mol, 60% oil dispersion washed with hexanes). The reaction was stirred for 1 hour at 0° C. to 5° C., 0.5 hour at room temperature and then quenched with acetic acid (1 mL). The resulting solution was concentrated and the residue dissolved in chloroform, washed with H2O, dried and concentrated. The residue was suspended in methanol (100 mL), treated with 1N sodium hydroxide at 0° C. and then stirred at room temperature for 2 hours. Acidification with 1N HCl (110 mL) and filtration gave 3.9 g of the desired product. An analytical sample was obtained by recrystallization from ethyl acetate; mp 183°–188° C.

EXAMPLE F

8-Ethenyl-6,7-difluoro-1-[1-(2,4-difluorobenzene)]-1,4-dihydro-4-oxo-3-quinolinecarboxylic acid This compound was prepared in a manner analogous to Example E. 2,4-Difluoro aniline was used in place of cyclopropylamine to provide the ethyl ester. Treatment with sodium hydroxide provided 0.71 g (20%, from 3-ethenyl-α-(ethoxymethylene)-2,4,5-trifluoro-β-oxo-benzene propionic acid, ethyl ester); mp 217°–219° C.

EXAMPLE G

3-Cyclopropyl-2,4,5-trifluorobenzoic acid

A mixture of 3-ethenyl-2,4,5-trifluoro benzoic acid, ethyl ester (0.5 g, 2.3 mmol), (N$^5$-cyclopentadienyl) dicarbonyl[(dimethylsulfonio)-methyl]iron tetrafluoroborate [*J. Org. Chem.*, 54, 2467, (1989)] (1.8 g, 4.6 mmol), and nitromethane (3 mL) was heated at refluxed for 20 hours. The resulting dark mixture was diluted with methylene chloride, filtered and concentrated to an oil. The oil was dissolved in hexane, filtered and concentrated to provide 0.33 g of the ester. This material was dissolved in methanol (5 mL) and 1N sodium hydroxide (1.8 mL). After stirring for 1 hour, the mixture was partitioned between H2O and ether, the aqueous layer was heated with charcoal, filtered and acidified with 1N HCl. The precipitate was filtered and dried to provide 0.17 g (38%) of the desired product; mp 95°–97° C.

EXAMPLE H

3-Bromo-2,5,6-trifluorobenzaldehyde

To a solution of 1-bromo-2,4,5-trifluoro benzene (25 g, 0.12 mol) in THF (200 mL at −78° C. was added LDA (80 mL, 1.5 M) dropwise. The mixture was stirred at −78° C. for 1 hour, then N-formylpiperidine (16 g, 0.144 mol) was added in one portion and stirring continued for 2 hours. An additional 15 g of N-formylpiperidine was then added every 0.5 hour in 5 g portions. The reaction was quenched with 3N HCl (pH 3) at −78° C. The reaction was warmed to 0° C. and partitioned between H$_2$O and ether. The ether layer was dried and concentrated and the residue was distilled to provide 13 g (45%) of the desired aldehyde; bp 63°–65° C. (0.2 mm).

EXAMPLE 1

1-Cyclopropyl-8-ethenyl-6-fluoro-1,4-dihydro-7-(3-methyl-1-piperazinyl)-4-oxo-3-quinolinecarboxylic acid A mixture of 1-cyclopropyl-8-ethenyl-6,7-difluoro-1,4-dihydro-4-oxo-3-quinolinecarboxylic acid (0.80 g, 2.9 mmol), 2-methylpiperazine (1.9 g, 19 mmol) and acetonitrile (5 mL) was heated at reflux for 22 hours. The mixture was cooled and concentrated. The residue was dissolved in H$_2$O (50 mL), treated with charcoal and filtered through celite. The pH of the filtrate was adjusted to 7, with HCl (3N) and after cooling to 0° C. the precipitate was collected and dried to provide 0.81 g (78%) of the desired product; mp 227°–231° dec.

EXAMPLE 2

1-Cyclopropyl-8-ethenyl-6-fluoro-1,4-dihydro-4-oxo-7-(1-piperazinyl)-3-quinolinecarboxylic acid A mixture of 1-cyclopropyl-8-ethenyl-6,7-difluoro-1,4-dihydro-4-oxo-3-quinolinecarboxylic acid (0.40 g, 1.44 mmol), piperazine (0.80 g, 7.8 mmol), and CH$_3$CN (3 mL) was refluxed for 16 hours. Workup was identical to that described in Example 1 to provide 0.28 g (54%) of the desired product; mp 213°–218° dec.

EXAMPLE 3

1-Cyclopropyl-8-ethenyl-7-[3(S)-(ethylamino)methyl-1-pyrrolidine]-6-fluoro-1,4-dihydro-4-oxo-3-quinolinecarboxylic acid This compound was prepared in a manner analogous to that described in Example 1, a yield of 0.32 g (63%) was obtained; mp 206°–208° C. The 3(S)-(ethylamino)-methyl-1-pyrrolidine was obtained as described in *J. Med. Chem.*, 30, 1711 (1987).

We claim:

1. A compound of the formula

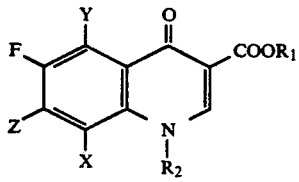

wherein X is alkenyl from two to ten carbon atoms, alkynyl from two to eight carbon atoms, cycloalkyl from three to six carbon atoms or cycloalkyl substituted by alkyl in which alkyl is one to four carbon atoms;

Y is hydrogen, fluoro or amino;

R$_1$ is hydrogen, alkyl of from one to six carbon atoms or a cation;

R$_2$ is alkyl of from one to four carbon atoms, vinyl, haloalkyl or hydroxyalkyl of from one to four carbon atoms, cycloalkyl of from three to six carbon atoms, phenyl or phenyl substituted by one or more halogen atoms;

Z is a secondary cyclic amino group of the formulae;

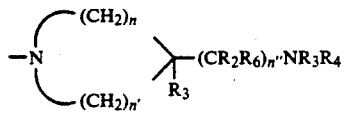

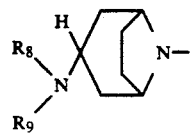

or

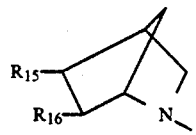

wherein n is 1, 2, 3, or 4;

n' is 1, 2, 3, or 4;

n+n' is a total of 2, 3, 4, or 5;

n" is 0, 1, or 2;

R$_3$ is hydrogen, alkyl of from one to four carbon atoms or a cycloalkyl of from three to six carbon atoms;

R$_4$ is hydrogen, alkyl of from one to four carbon atoms, hydroxyalkyl of from two to four carbon atoms, trifluoroethyl, or R'$_4$CO wherein R'$_4$ is alkyl of from one to four carbon atoms, or alkoxy of from one to four carbon atoms;

R$_5$ and R$_6$ are each independently hydrogen or alkyl of from one to three carbon atoms;

R$_8$ and R$_9$ are each independently hydrogen, alkanoyl of from one to three carbon atoms, alkyl of from one to three carbon atoms, isopropyl or cyclopropyl;

R$_{15}$ and R$_{16}$ are each independently hydrogen, halogen, NR$_{17}$R$_{18}$, OR$_{17}$, SR$_{17}$, alkyl or form one to three carbon atoms, wherein R$_{17}$ and R$_{18}$ are each independently hydrogen, alkyl of from one to three carbon atoms, or acyl of from one to three carbon atoms;

or a pharmaceutically acceptable acid addition salt thereof.

2. A compound according to claim 1 wherein Y is hydrogen or amino, and R$_2$ is ethyl, vinyl, 2-fluoroethyl, difluoroethyl, cyclopropyl, pehnyl, 2-fluorophenyl, 4-fluorophenyl or 2,4-difluorophenyl.

3. A compound according to claim 2 wherein Z is

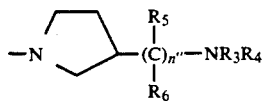

wherein R₃ is hydrogen, methyl, ethyl, n-propyl, or 2-propyl, R₅ and R₆ are hydrogen, methyl, or ethyl and n" is 0 or 1.

4. A compound according to claim 3 wherein R₁ is hydrogen or a cation.

5. A compound according to claim 4, wherein n" is zero or one; R₃, R₅, and R₆ are hydrogen, methyl, ethyl, or n-propyl, and R₄ is hydrogen.

6. A compound according to claim 5, wherein Z is

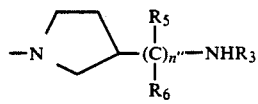

wherein R₁ is hydrogen; R₂ is ethyl, vinyl, 2-fluoroethyl, cyclopropyl or 2,4-difluorophenyl; R₃ is hydrogen, methyl, ethyl, 1-propyl or 2-propyl, and R₅ and R₆ are hydrogen or methyl.

7. A compound according to claim 6, wherein Z is

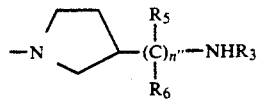

in which n" is 0 or 1; R₂ is cyclopropyl; R₃ is hydrogen, methyl, ethyl, 1-propyl or 2-propyl, and R₅ and R₆ are hydrogen or methyl.

8. A compound according to claim 7, wherein X is alkenyl of two to ten carbon atoms, alkynyl of two to eight carbon atoms or cycloalkyl of three to six carbon atoms.

9. A compound according to claim 8, wherein X is alkenyl of two to four carbon atoms, alkynyl of two or three carbon atoms, cyclobutyl or cyclopropyl.

10. A compound according to claim 9, wherein X is ethenyl, ethynyl or cyclopropyl.

11. A compound according to claim 10 and being 1-cyclopropyl-8-ethenyl-7-[3(S)-(ethylamino)-methyl-1-pyrrolidine]-6-fluoro-1,4-dihydro-4-oxo-3-quinolinecarboxylic acid.

12. A pharmaceutical composition comprising an antibacterially effective amount of a compound as claimed in claim 1 together with a pharmaceutically acceptable carrier.

13. A method of treating bacterial infections in mammals which comprises administering to said mammal a pharmaceutical composition as claimed in claim 12 in unit dosage form.

* * * * *